United States Patent
Hasan

(10) Patent No.: US 6,999,164 B2
(45) Date of Patent: *Feb. 14, 2006

(54) MEASUREMENT SYSTEM CLUSTER

(75) Inventor: Talat Fatima Hasan, Saratoga, CA (US)

(73) Assignee: Tokyo Electron Limited, Tokyo (JP)

( * ) Notice: Subject to any disclaimer, the term of this patent is extended or adjusted under 35 U.S.C. 154(b) by 530 days.

This patent is subject to a terminal disclaimer.

(21) Appl. No.: 10/132,538

(22) Filed: Apr. 24, 2002

(65) Prior Publication Data

US 2002/0176074 A1 Nov. 28, 2002

Related U.S. Application Data

(60) Provisional application No. 60/286,485, filed on Apr. 26, 2001.

(51) Int. Cl.
*G01N 21/00* (2006.01)

(52) U.S. Cl. ............................ 356/237.4; 356/237.5; 700/121

(58) Field of Classification Search .. 356/237.1–237.5, 356/394; 702/35; 700/121; 438/14
See application file for complete search history.

(56) References Cited

U.S. PATENT DOCUMENTS

| | | | |
|---|---|---|---|
| 5,393,624 A | 2/1995 | Ushijima | 430/30 |
| 5,442,416 A | 8/1995 | Tateyama et al. | 354/319 |
| 5,492,594 A | 2/1996 | Burke et al. | 216/86 |
| 5,616,063 A | 4/1997 | Okumura et al. | 451/1 |
| 5,695,601 A | 12/1997 | Kodera et al. | 156/636.1 |
| 5,909,276 A * | 6/1999 | Kinney et al. | 356/237.2 |
| 5,948,203 A | 9/1999 | Wang | 156/345 |
| 6,028,664 A | 2/2000 | Cheng et al. | |
| 6,157,450 A | 12/2000 | Marchese-Ragona et al. | 356/376 |
| 6,166,801 A | 12/2000 | Dishon et al. | 355/27 |
| 6,368,181 B1 | 4/2002 | Dvir et al. | 451/6 |
| 6,556,947 B1 | 4/2003 | Scheiner et al. | 702/172 |
| 6,701,259 B1 * | 3/2004 | Dor et al. | 702/35 |
| 2002/0090744 A1 | 7/2002 | Brill et al. | 438/11 |
| 2002/0165636 A1 * | 11/2002 | Hasan | 70/121 |

OTHER PUBLICATIONS

G. Dishon et al., "Dielectric CMP Advanced Process Control Based on Integrated Thickness Monitoring," *CMP-MIC Conference 1998 IMIC*, vol. 300P, Feb. 19-20, 1998, pp. 267-274.

G. Dishon et al., "On-Line Integrated Metrology for CMP Processing," *CMP-MIC Conference 1996 ISMIC*, vol. 100P, Feb. 22-23, 1996, pp. 273-276.

G. Dishon et al. "Monitoring Choices of CMP Planarization Processes," Reprinted from: *VMICSpecialty Conference, 2nd International CMP Planarization Conference*, Santa Clara, California, Feb. 13-14, 13 pages in length.

International Search Report dated Aug. 28, 2002 for PCT/US02/13158 filed Apr. 24, 2002.

* cited by examiner

*Primary Examiner*—Hoa Q. Pham
(74) *Attorney, Agent, or Firm*—Stallman & Pollock LLP

(57) ABSTRACT

Systems and methods are disclosed for measuring semiconductor wafers in a fabrication process using one or more of a plurality of measurement systems. A measurement system cluster is provided having a plurality of such measurement systems, along with a system for transferring wafers to one or more of the measurement systems according to one or more selection criteria. Measurement systems may be selected for use based on availability and throughput capabilities, whereby overall system throughput and efficiency may be improved within the required accuracy capabilities required for measuring process parameters associated with the wafers.

18 Claims, 8 Drawing Sheets

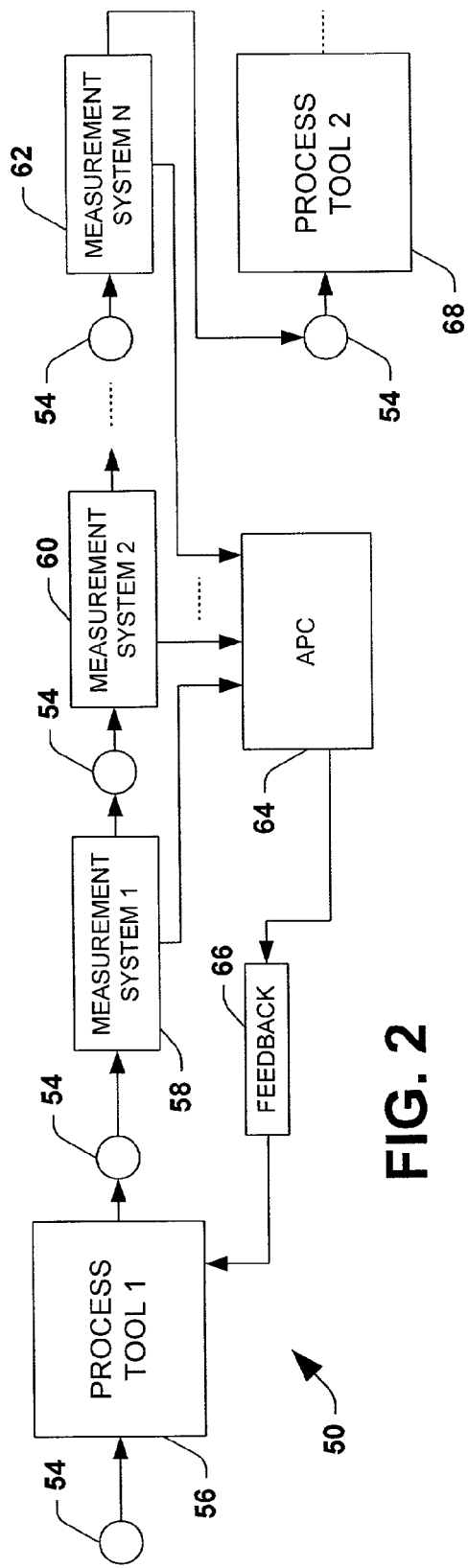
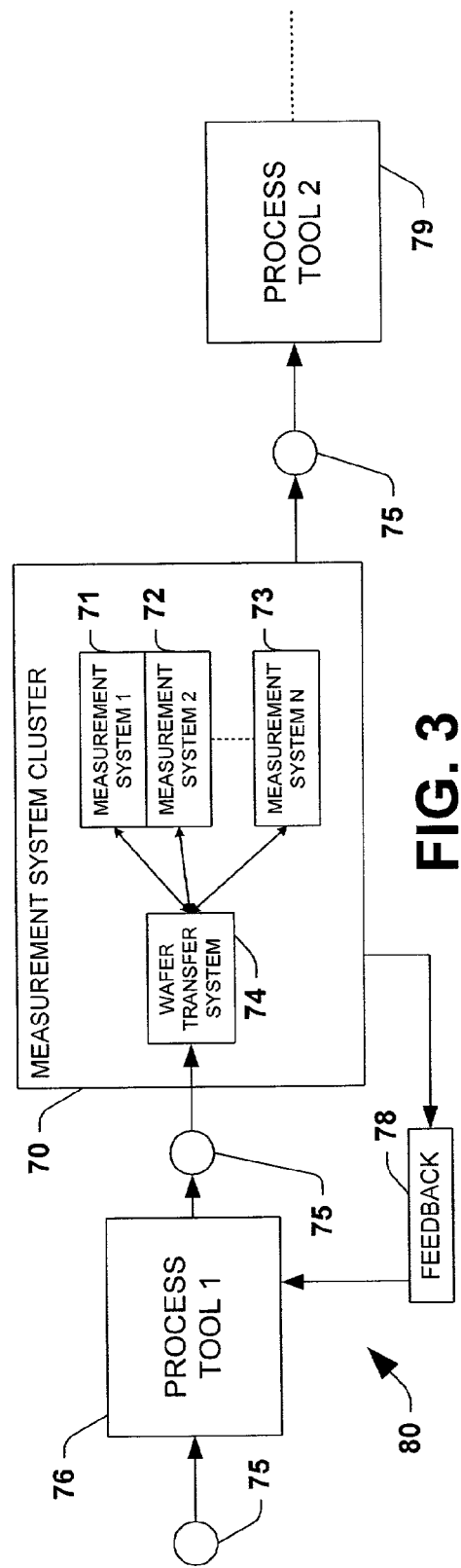
FIG. 2
FIG. 3

MEASUREMENT SYSTEM CLUSTER

CROSS REFERENCE TO RELATED APPLICATION

This application claims the benefit of U.S. Provisional Application Ser. No. 60/286,485, entitled "Measurement System Cluster" and filed on Apr. 26, 2001, the entirety of which is incorporated herein by reference.

TECHNICAL FIELD

The present invention relates to the art of semiconductor device manufacturing and fabrication, and more particularly to systems and methodologies for measuring process parameters associated with processed semiconductor wafers.

BACKGROUND OF THE INVENTION

In the semiconductor industry there is a continuing trend toward higher device densities. To achieve these high densities there have been, and continue to be, efforts toward scaling down the device dimensions on semiconductor wafers. In order to accomplish such a high device packing density, smaller feature sizes are required. These may include the width and spacing of interconnecting lines and the surface geometry such as the corners and edges of various features.

The requirement of small features with close spacing between adjacent features requires high-resolution photolithographic processes as well as high resolution metrology and inspection instruments and systems. In general, lithography refers to processes for pattern transfer between various media. It is a technique used for integrated circuit fabrication in which, for example, a silicon wafer is coated uniformly with a radiation-sensitive film (e.g., a photoresist), and an exposing source (such as ultraviolet light, x-rays, or an electron beam) illuminates selected areas of the film surface through an intervening master template (e.g., a mask or reticle) to generate a particular pattern. The exposed pattern on the photoresist film is then developed with a solvent called a developer which dissolves either the exposed or unexposed depending on the type of photoresist (i.e., positive or negative resist, thus leaving a photoresist pattern corresponding to the desired pattern on the silicon wafer for further processing.

In addition to lithographic processes, other process steps in the fabrication of semiconductor wafers require higher resolution processing and inspection equipment in order to accommodate ever shrinking feature sizes and spacing. Measurement instruments and systems are used to inspect semiconductor devices in association with manufacturing production line quality control applications as well as with product research and development. The ability to measure and/or view particular features in a semiconductor workpiece allows for adjustment of manufacturing processes and design modifications in order to produce better products, reduce defects, etc. For instance, device measurements of critical dimensions (CDs) and overlay registration may be used to make adjustments in one or more such process steps in order to achieve the desired product quality. Accordingly, various metrology and inspection tools and instruments have been developed to map and record semiconductor device features, such as scanning electron microscopes (SEMs), atomic force microscopes (AFMs), scatterometers, spectroscopic ellipsometers (SEs), and the like. Scatterometers, as used in this context, are optical instruments that employ algorithms to invert the parameters of a grating from the measured optical characteristics. Typically, scatterometers are used to measure gratings with lateral dimensions that are finer than wavelengths employed by the instrument. The fundamental optical instrument for a scatterometer may be identical to optical instruments used, e.g., for thin-film metrology. Thus an SE, which is routinely used to characterize thin (unpatterned) films, may be employed as a scatterometer if the appropriate algorithms are available. The same would be true of a reflectometer. In some cases, the optical instrument portion of a scatterometer may be specifically designed for scatterometry. In what follows, "SE" is used to designate a spectroscopic ellipsometer used for standard thin film measurements, i.e., film thickness and/or optical properties.

Such measurement instruments are typically employed in stand-alone, off-line fashion, for example, wherein one or more wafers processed by a particular process tool are measured or inspected and a determination is made as to whether measured process parameters (e.g., CDs, overlay registration, film thicknesses, material properties, particle count) are within acceptable limits, and/or whether process related defects are present in the wafers. A stand-alone measurement instrument is not integrated into a process tool, and thus can be used to service multiple process tools. The measurements or inspection may be performed using more than one such measurement instrument, where features are measured using different instruments. Because the measurement instruments are stand-alone systems, the wafers must be transported between the process tool and the measurement instruments before a measurement can be obtained. The stand-alone nature of conventional measurement instrumentation and the resulting transport of wafers between such instruments results in significant down-time in a semiconductor fabrication facility, wherein expensive process tools are shut down pending a final determination as to the existence of problems in the process.

In addition, where wafers must be measured in two or more successive measurement systems in serial fashion, the measurement instrument having the lowest wafer throughput capacity becomes a bottleneck for the inspection process, thus further exacerbating process down-time. Moreover, existing measurement or inspection instruments for semiconductor wafer fabrication processes may provide different results for measurement of the same feature, wherein one instrument may identify a dimensional problem associated with a particular feature, while another such instrument may not. Thus, there is a need for improved measurement systems and methodologies which provide for timely, consistent feature measurement and inspection for wafers being processed in a fabrication facility, and which reduce or mitigate process down-time.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter. The present invention provides systems and methods for measuring and inspecting semiconductor wafers in a fabrication process using one or more of a plurality of measurement instruments or metrology tools by which the aforementioned shortcomings associated with prior systems may be mitigated. Clustered measurement systems are provided having a plurality of measurement instruments, together with systems for transferring wafers to one or more of the measurement devices according to selection criteria. Measurement systems may accordingly be selected for use based on availability, throughput, capabilities and/or other considerations, whereby overall system throughput and efficiency may be improved within the accuracy capabilities required for measuring process parameters (e.g., such as CDs, overlay registration, or the like) associated with the wafers.

In addition, the present invention facilitates correlation or cross-calibration between data responses of at least two measurement systems, such as for example a CD-SEM and a scatterometer. In particular, a wafer (e.g., one or more layers in layer stack) may be measured with a scatterometer to receive a data response associated with the scattering of an incident wavelength of light. The wafer may also be measured by a CD-SEM to receive another data response, which is characteristic of the CD-SEM device. The data responses from the scatterometer and the CD-SEM may be correlated. Based on the correlation, the scatterometer can be adjusted to the extent that future measurements taken by a scatterometer resemble data responses as if produced by a CD-SEM. This correlation facilitates alternating or varying between the measurement system employed depending on the processing time, costs, accuracy and efficiency needs and requirements.

According to one aspect of the present invention, a measurement system cluster is provided having two or more measurement instruments such as scanning electron microscopes (SEMs), atomic force microscopes (AFMs), scatterometers, spectroscopic ellipsometers (SEs), or the like, which can be selectively employed to measure process parameters associated with a wafer. The various instruments may be interconnected to share information, such as calibration information, and can be cross-calibrated. The metrology cluster further comprises a wafer transfer mechanism or system, such as a robot, operative to selectively provide a wafer to one or more of the measurement devices according to at least one measurement system selection criterion. The selection criteria, for example, may take into account the capabilities, availability, and throughput of the various measurement instruments, whereby a selected measurement device has appropriate measurement capabilities required for a given wafer (e.g., or set of wafers being processed), such that an available measurement instrument having the highest throughput capacity can be selected for use in performing the required measurements.

In addition, the present invention facilitates correlation or cross-calibration between measurements of at least two measurement systems, such as for example a CD-SEM and a scatterometer. In particular, multiple reference samples, e.g., a particular site in different dies on a reference wafer, may be measured with a scatterometer. The reference sites may also be measured by a CD-SEM. The measurements from the scatterometer and the CD-SEM may be correlated. Based on the correlation, future scatterometer measurements, e.g., on production samples, can be adjusted to resemble measurements that would be produced by a CD-SEM. This correlation facilitates alternating or varying between the measurement system employed depending on the processing time, costs, accuracy and efficiency needs and requirements.

Another aspect of the invention provides a wafer measurement or inspection system having a measurement instrument operative to measure at least one process parameter associated with a wafer, as well as an optical character recognition (OCR) system providing a wafer identification according to at least one optically recognizable character on the wafer. A character in this context is taken as an indicator of information. For examples, characters may be alphanumeric or a bar code. The OCR system may thus read stampings or markings, such as lot numbers, data codes, and other character-based indicia on the wafer being measured, and provide for selection of measurement instruments appropriate for the required measurement task. The measurement system, moreover, may be integral with one or more process tools forming a part of the fabrication process, whereby processed wafers are provided directly to the system without further machine or human intervention.

In accordance with yet another aspect of the invention, there is provided a methodology for measuring process parameters associated with a wafer in a semiconductor fabrication process. Wafers are received from the fabrication process and selectively provided to one or more measurement instruments according to a measurement system selection criteria. In this regard, the selection criteria can include using an available measurement instrument having the highest throughput capacity and the required accuracy or other performance capabilities required for the wafer measurements, whereby the overall throughput of a system can be improved. The method may further include identifying the wafer being measured, such as for example, through reading one or more optical characters on the wafer, determining measurement capabilities required to measure the process parameter according to the identity of the wafer, and selecting the appropriate measurement instrument according to the required measurement capabilities and measurement system capabilities information associated with the available measurement devices.

To the accomplishment of the foregoing and related ends, the invention, then, comprises the features hereinafter filly described. The following description and the annexed drawings set forth in detail certain illustrative implementations of various aspects of the invention. However, these implementations are indicative of but a few of the various ways in which the principles of the invention may be employed. Other aspects, advantages and novel features of the invention will become apparent from the following detailed description of the invention when considered in conjunction with the drawings.

BRIEF DESCRIPTION OF THE DRAWINGS

FIG. 2 is a schematic diagram illustrating a fabrication process having process tools and stand-alone measurement systems;

FIG. 3 is a schematic diagram illustrating a fabrication process having an exemplary measurement system cluster in accordance with the invention;

DETAILED DESCRIPTION OF THE INVENTION

Figure 1:
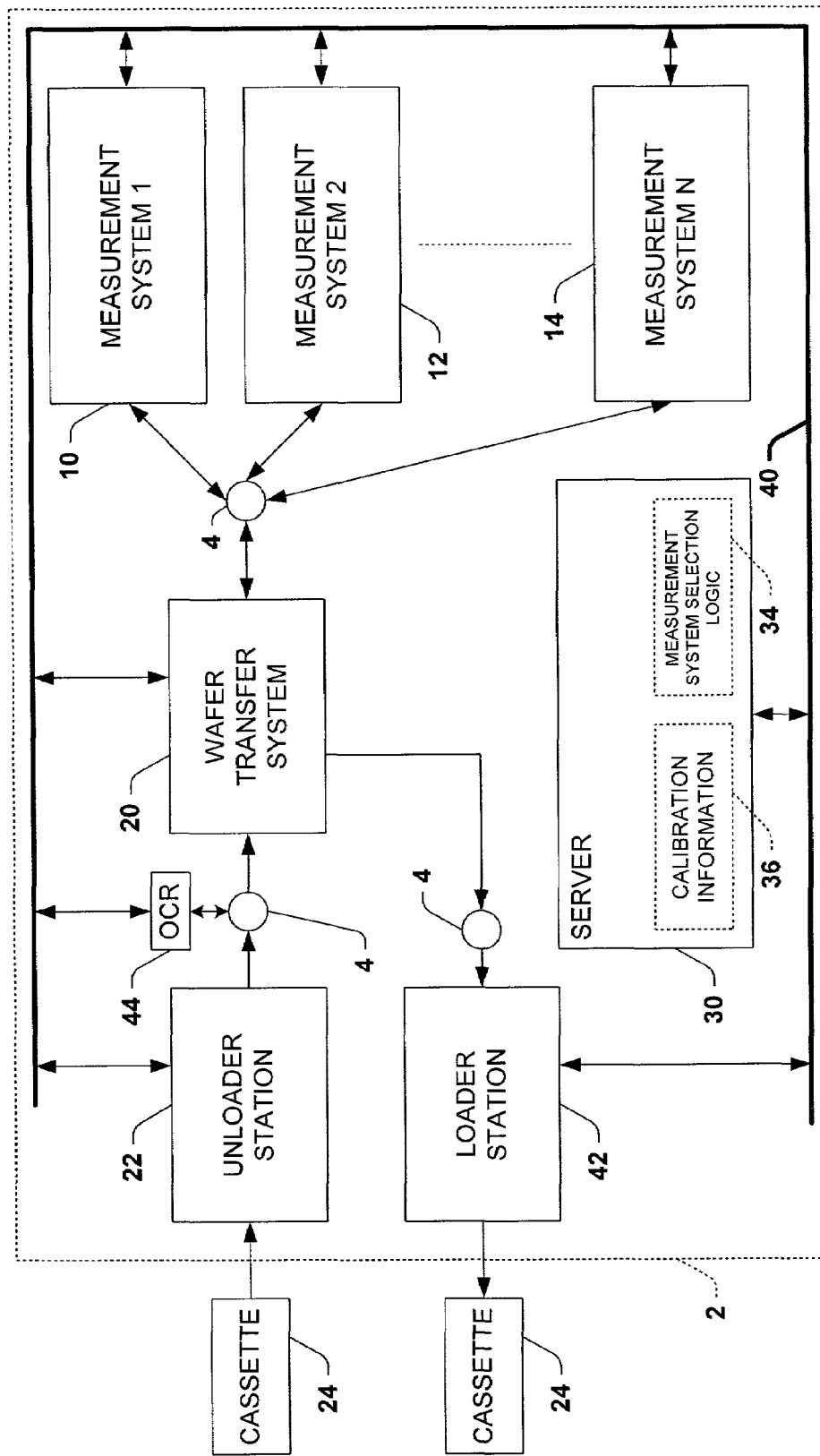
FIG. 1 is a schematic diagram illustrating an exemplary measurement system cluster in accordance with one or more aspects of the present invention.

The various aspects of the present invention will now be described with reference to the drawings, wherein like reference numerals are used to refer to like elements throughout. The invention provides systems and methods for measuring and/or inspecting semiconductor wafers in a fabrication process using one or more of a plurality of measurement instruments or systems. A measurement system cluster is provided having a plurality of such measurement systems, together with a system for transferring wafers to one or more of the measurement systems according to one or more selection criteria. Measurement instruments or systems may be selected for use based on availability and throughput capabilities, whereby overall equipment throughput and efficiency can be improved within the accuracy capabilities required for measuring process parameters associated with the wafers.

In FIG. 1, an exemplary measurement system cluster 2 is illustrated in which various aspects of the present invention may be implemented. The cluster 2 may be advantageously employed for measuring process parameters (e.g., overlay registration, photoresist layer defects, feature sizes, spacing between features, particle defects, chemical defects, and the like) associated with wafer 4 in a semiconductor fabrication process. The measurement system cluster 2 comprises a plurality of measurement systems 10, 12, and 14 having measurement instruments (not shown) associated therewith. For example, the systems 10, 12, and 14 may include scanning electron microscopes (SEMs), atomic force microscopes (AFMs), scatterometers, spectroscopic ellipsometers (SEs), or other measurement instruments adapted to measure process parameters associated with processed semiconductor wafers 4.

The cluster 2 further comprises a wafer transfer system 20, such as a robot or other automated wafer translation device, which receives wafers 4 processed in the fabrication process via an unloader station 22 which unloads wafers 4 from a cassette 24 or other wafer carrying device. The wafer transfer system 20 then selectively provides the wafers 4 to one or more of the measurement systems 10, 12, and/or 14 according to a measurement system selection criteria as described in greater detail hereinafter. One or more process parameters (not shown) are then measured and/or inspected in order to verify proper processing of the wafers and/or to detect defects or errors in the fabrication process. The exemplary cluster system 2 further comprises a computer system 30 having a measurement system selection logic 34, and calibration information 36 therein. The measurement systems 10, 12, and 14, as well as the unloader station 22, the wafer transfer system 20, and the computer system 30 are networked together via a network 40, whereby measurement information, measurement system selection information, calibration information 36, and other control information and data may be shared between the various components of the measurement system cluster 2.

Once the appropriate process parameters associated with the wafers 4 have been measured via the measurement systems 10, 12, and/or 14, the wafer transfer system 20 provides the wafers 4 to a loader station 42 which loads the wafers into outgoing wafer cassettes 24 for transfer to other systems in the fabrication process, such as a downstream process tool (not shown). There are many alternative arrangements, each having different strategies for loading and unloading wafers. For instance, the stations 22 and/or 42 can be loader/unloader stations, able to perform both functions. With a loader/unloader station, wafers may be returned after measurement to the same cassette in which they arrived. In addition, cluster 2 may have a single loader/unloader, or more than two; and/or cluster 2 may have more than one each of load and/or unload stations.

The cluster 2 further comprises an optical character recognition (OCR) system 44 providing a wafer identification (not shown) to the measurement system selection logic component 34 via the network 40, whereby the component 34 may make an appropriate selection of measurement system(s) 10, 12, and/or 14 to be used to measure or inspect the wafer 4. Although the exemplary cluster 2 identifies the wafers 4 using the OCR system 44, other techniques may be used to identify the wafers 4, such as for example, location within the cassette 24, or other methods as are known. It will be appreciated, however, that where lot code information, date codes, and the like are printed or stamped directly on the wafers 4, the OCR system 44 advantageously reduces the likelihood of incorrect wafer identification.

Figure 8:
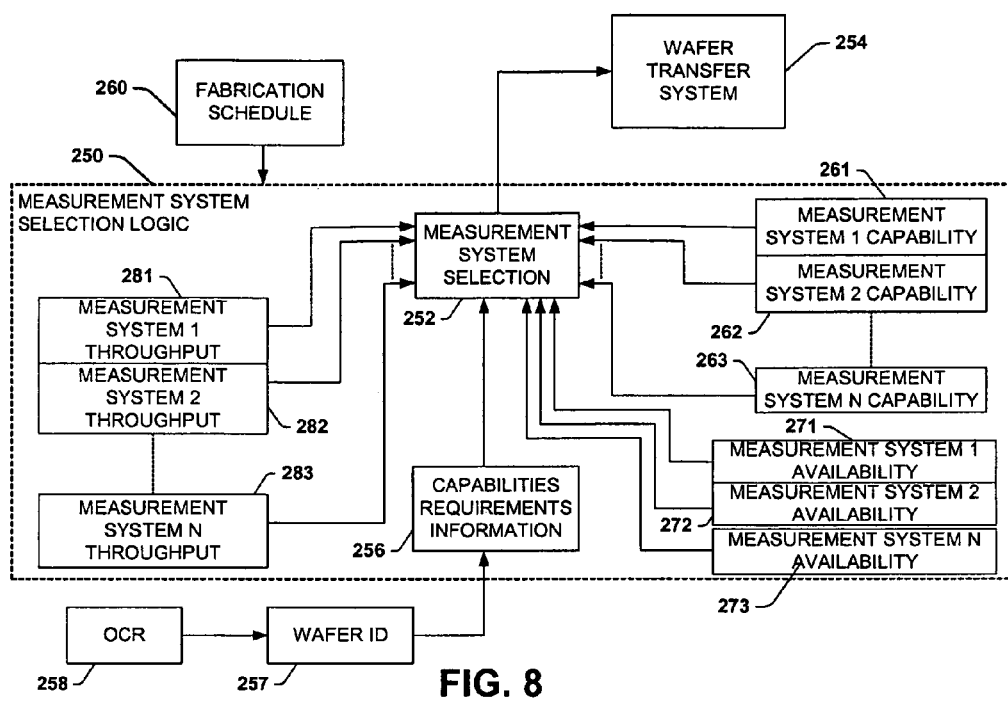
FIG. 8 is a schematic diagram illustrating an exemplary measurement system selection logic component according to another aspect of the invention.

The measurement system selection logic component 34 in the computer system 30 provides a measurement system selection to the wafer transfer system 20 according to one or more selection criteria (e.g., as illustrated and described in greater detail hereinafter with respect to FIG. 8), wherein the wafer transfer system 20 provides the wafers 4 to at least one of the measurement systems 10, 12, and/or 14 according to the measurement system selection. For example, the measurement system selection criteria can include capabilities requirements information associated with the wafer 4, as well as capability information, availability information, and throughput information associated with the measurement systems 10, 12, and 14. The selection moreover, may be made according to a desired sequencing of measurements in the systems 10, 12, and/or 14.

The capabilities information may thus be derived according to the wafer identification from the OCR system 44, and may comprise information indicating the type of feature(s) or dimension(s) to be measured in the system 2, as well as the required accuracy for the measurement(s). The measurement system selection from the logic component 34 may further take into account the measurement capabilities of the various measurement systems 10, 12, and/or 14. For example, one or more of the systems 10, 12, and/or 14 may be capable of performing a given measurement within the required accuracy, while others may not. In addition, the respective systems 10, 12, and/or 14 can each have different throughput capabilities. For instance, a SEM instrument may be able to measure 30 wafers per hour (wph), a scatterometer may measure up to 150 wph, and a spectroscopic ellipsometer may measure 75 to 80 wph. In selecting a measurement system to perform a given measurement task, therefore, the measurement system selection logic component 34 may advantageously select the system which can provide the highest throughput, within the required measurement capabilities for the measurement.

In this regard, the selection logic component 34 may also consider which systems 10, 12, and/or 14 are currently available in scheduling the transfer of wafers 4 via the transfer system 20. Thus, the measurement system selection logic component 34 provides the selection indicating a selected measurement system 10, 12, or 14 having capabilities required for the wafer 4 according to the capabilities requirements information (e.g., obtained or derived from the wafer identification via the OCR system 44) and the measurement system capability information. Furthermore, the selection may reflect the measurement system having the highest throughput with the capabilities required for the wafer 4 according to the measurement system availability information and the throughput information.

As the various measurement systems 10, 12, and 14 are interconnected in the cluster 2, and may share information via the network 40, the systems 10, 12, and/or 14 may be cross-calibrated. In this regard, the calibration information 36 in the computer system 30 may be shared between the various systems 10, 12, and 14, whereby the measurements made by one measurement instrument in the systems 10, 12, or 14, are comparable to those made by another such instrument. The exemplary cluster system 2 thus provides significant advantages over conventional stand-alone measurement systems with respect to cross-calibration as well as in reducing excess transferring of the wafers 4 between such stand-alone measurement stations in a fabrication process.

Information may be provided to an upstream (e.g., or downstream) process tool (e.g., photo-resist track, stepper, or the like), which can employ such information as process feedback (or feed forward), whereby on-line closed-loop process control can be achieved, for example, wherein the process tool performs fabrication processing steps according to the measurement data in order to mitigate defects in processed wafers 4. Alternatively or in combination, the measurement (e.g., and/or defect detection) information may be provided to an advanced process control (APC) system (not shown), which in turn may provide process adjustments to such process tools in feedback and/or feed forward fashion. In this regard, it will be appreciated that the reduction in transfer time resulting from clustering of multiple measurement systems 10, 12, and 14 into a single system 2, as well as the selective employment of appropriate measurement systems based at least in part on throughput and/or availability information, may be used to mitigate down-time of related process tools, whereby real-time or near real-time measurement and/or defect detection may be achieved with little or no fabrication process down-time, in accordance with the present invention. Moreover, the exemplary measurement cluster 2 may also be integrated with a process tool, as illustrated further in FIGS. 6 and 7, which operates to perform one or more fabrication processing steps on the wafers 4 and to provide the processed wafers 4 to the wafer transfer system 20.

Referring briefly to FIG. 2, a portion of a conventional wafer fabrication process 50 is illustrated in which wafers 54 proceed in serial fashion from a first process tool 56 to a series of measurement instrument systems 58, 60, and 62. The systems 58, 60, and 62 provide measurement information to an APC system 64, which in turn provides feedback information 66 (e.g., such as a process adjustment or control information) to the process tool 56. Thereafter, the wafers 54 are provided to a second (e.g., downstream) process tool 68. As can be seen in FIG. 2, the APC system 64 is unable to provide timely feedback to the process tool 56 because the measurements from the measurement systems 58, 50, and 62 are not made at the same time, and further because the wafers 54 must be transported (e.g., typically manually) between the systems 58, 60, and 62.

Referring now to FIG. 3, the invention provides clustering of measurement instruments or systems 71, 72, and 73 into a measurement system cluster 70 along with a wafer transfer system 74, wherein the cluster or system 70 may receive wafers 75 from an upstream process tool 76 in a fabrication process 80, typically in a cassette or FOUP. The system 70 may operate in a manner similar to the operation of the exemplary cluster 2 of FIG. 1, whereby the wafer transfer system 74 selectively provides the wafers 75 from the process tool 76 to one or more of the measurement systems or instruments 71, 72, and/or 73 according to one or more measurement system selection criteria. The measurement system selection criteria may include, for example, measurement capabilities, measurement capability requirements, availability, anticipated need based on scheduling of fabrication process 80 and/or throughput capabilities. The time savings achieved by the clustering of the measurement systems 71–73 and the operation of the wafer transfer system 74 in selecting an appropriate measurement system for a particular inspection task allows timely provision of measurement information (e.g., overlay registration, CD measurements, feature size and spacing) for feedback 78 to the process tool 76 in a timely fashion, whereby the down-time associated with process parameter measurement in conventional systems (e.g., FIG. 2) can be advantageously mitigated in accordance with the present invention. Once measured, the wafers 75 can then be provided from the measurement system cluster 70 to a second (e.g., downstream) process tool 79. Although not shown, the measurement information may be used for feed forward, e.g., to downstream process tool 79. System 70 provides the same advantages over a series of measurement instrument systems 58, 60, and 62, as shown in FIG. 2, when used for feed forward or feedback information.

Figure 4:
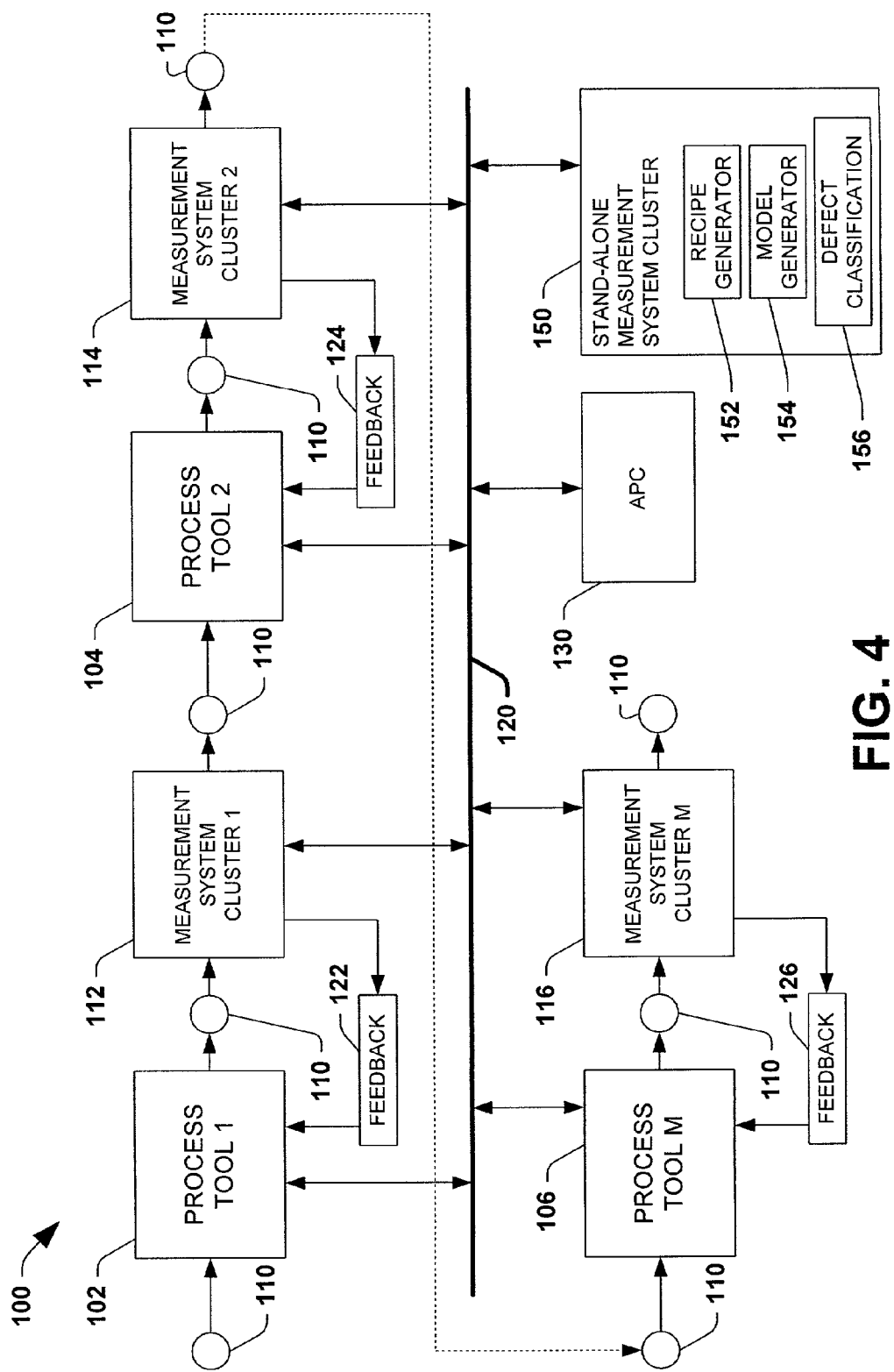
FIG. 4 is a schematic diagram illustrating a semiconductor wafer fabrication process employing measurement system clusters providing measurement information as feedback to associated process tools, as well as to an advanced process control system according to the invention.

Another semiconductor device fabrication process 100 is illustrated in FIG. 4, in which other advantages of the present invention are shown. The process 100 comprises process tools 102, 104, and 106 and associated measurement system clusters 112, 114, and 116, respectively, which operate to measure one or more process parameters associated with wafers 110 in a manner similar to the exemplary system 2 of FIG. 1. Any of measurement system clusters 112, 114, and 116 may be a cluster of one measurement system. Further, the association of a cluster with a tool, e.g., cluster 112 to tool 102, can be integrated into the tool, where the cluster shares support, wafer transport and/or other facilities. The measurement system clusters 112, 114, and 116, as well as the process tools 102, 104, and 106 communicate with each other via a network 120, whereby information may be transferred therebetween. An APC system 130 is also operatively connected to the network 120, such that measurement information (e.g., CDs, overlay registration, and the like) may be obtained from the measurement systems 112, 114, and 116 for providing process feedback or process feed forward or adjustments to the various process tools 102, 104 and/or 106 and for other processing of such measurement information. For example, the APC system 112, may provide defect classifications to one or more of the process tools 102, 104, and/or 106, whereby adjustments may be made therein, in order to reduce the number of such defects in the fabrication process 100.

The measurement system clusters 112, 114, and 116 can also include APC systems therein, providing feedback information 122, 124, and 126, respectively to the process tools 102, 104, and 106, for timely adjustment of the individual process tools 102, 104, and 106, and the respective process steps carried out therein. Alternatively or in combination, such feedback information may be provided from the measurement system clusters 112, 114, and/or 116 to one or more of the process tools 102, 104, and/or 106 via the network 120. In addition, the invention provides for sharing of calibration information between the clusters 112, 114, and/or 116, whereby the clusters 112, 114, and/or 116 and/or the component measurement instrument systems therein, may be cross-calibrated, such that the measurements made thereby are performed according to a universal standard across the entire process 100. The universal standard may apply over a larger domain than just process 100, e.g., within a whole manufacturing facility, or even linking manufacturing facilities.

The process 100 can further include a standalone measurement system cluster 150 networked with the clusters 112, 114, and 116 via network 120. For example, clusters 112, 114, or 116 may be integrated within their associated tools, as described above, and primarily measure wafers 110 processed by their associated tool, whereas cluster 150 is set up for measuring wafers from many sources with ease. Furthermore, cluster 150 may comprise measurement instruments (not shown) of types found in the clusters 112, 114, and 116 as well as a recipe generator 152, a database generator 154 and a defect classification system 156. Recipes are sets of instructions for a measurement instrument comprising where to measure on the wafer, measurement system parameters for the physical measurement, and specification of an algorithm to convert the fundamental physical measurements into useful information. For example, for a reflectometer measurement instrument, the recipe may comprise information about the layout of the wafer including die size and location, which dies on the wafer to measure, one or more sites within the die at which to measure (typically referenced to structures in the die), pattern recognition parameters to identify and locate the structures in the die, the length of time to integrate over for measuring reflected intensities, the wavelengths of light at which to report measured intensities, an algorithm based on model that comprises a stack of thin films at the measurement location, specification of which parameters are known and which are to be measured, etc. The recipe may comprise much more information than cited in this example. Instruments of a different nature than the exemplary reflectometer may require rather different information in their appropriate recipes.

In general, databases contain information to aid in the conversion of the fundamental physical information collected by an instrument into useable information about the process state of the wafer. As an example, a database for a reflectometer from database generator 154 can aid in converting measured optical absolute reflectivities to CD or film thickness. Algorithms use databases, e.g., for scatterometry, when the computational time for an algorithm is excessive, and it is useful to store partial results of the algorithm in a database for later, accelerated use. The cluster 150 can be employed to generate databases and/or recipes for the measurement and/or inspection of wafers by the instruments of the in-process measurement system clusters 112, 114, and/or 116, which may be uploaded thereto through the networks 120. In this manner, the standalone cluster 150 may be advantageously employed to perform setup operations (e.g., recipe and/or database generator) for use in the in-process clusters 112, 114 and/or 116, while the clusters 112, 114, 116 are in use measuring processed wafers.

Figure 5:
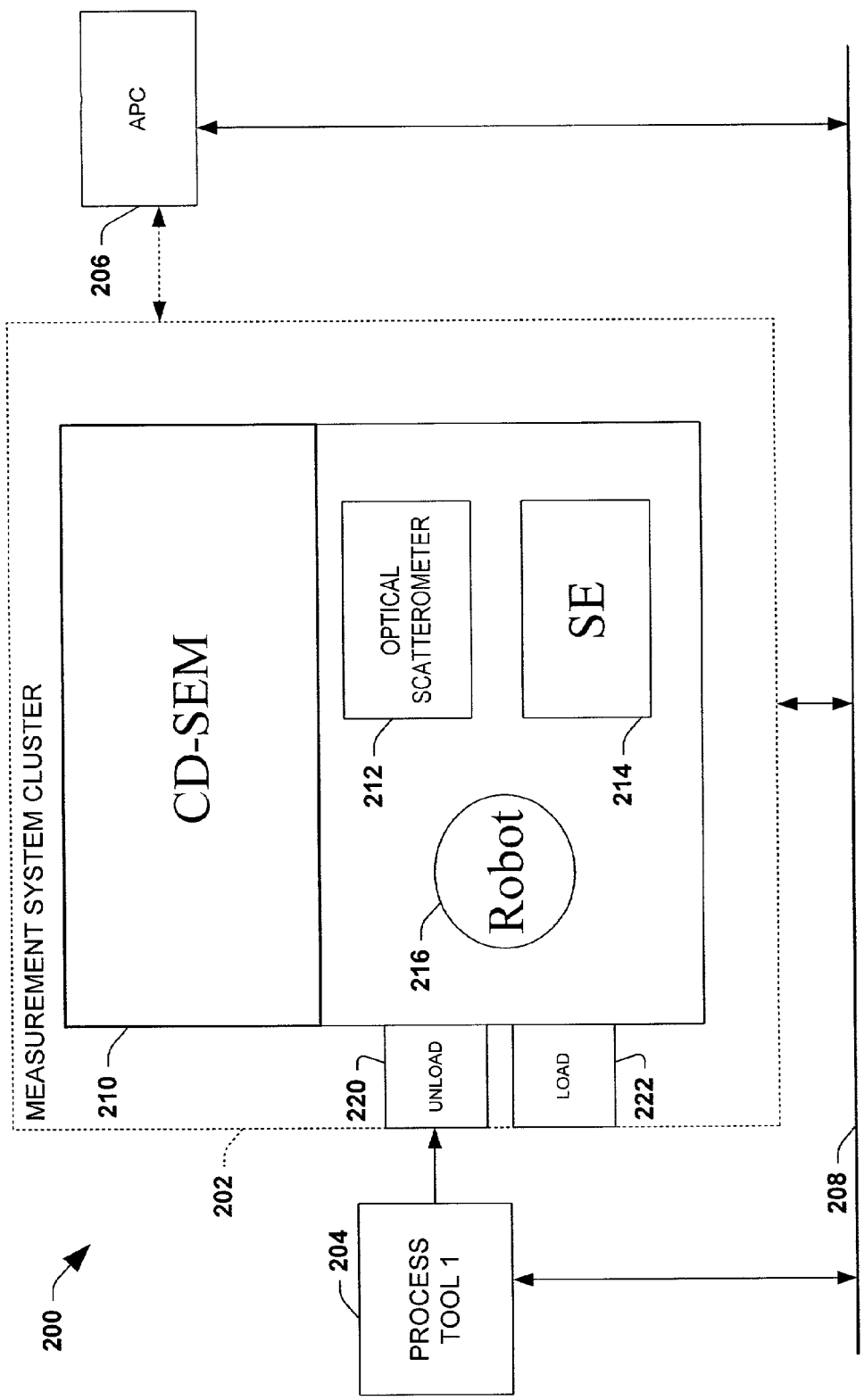
FIG. 5 is a schematic diagram illustrating another exemplary measurement system cluster operatively associated with a process tool and an advanced process control system.

Referring now to FIG. 5, another exemplary implementation of the present invention is illustrated, wherein a measurement system cluster 202 is part of a fabrication process 200 having a process tool 204 and an APC system 206. The systems 202 and 206, as well as the process tool 204 may communicate with each other via a network 208. Alternatively or in combination, the APC system 206 can communicate directly with the measurement system cluster 202. The measurement system cluster 202 is employed in the process 200 for measuring process parameters associated with wafers (not shown) transferred thereto from the process tool 204 in a manner similar to the exemplary system 2 of FIG. 1. The system 202 includes a scanning electron microscope (CD-SEM) system 210 operative to measure process parameters of the wafers, which may also comprise pumps and sealing devices (not shown) for creating a vacuum therein. The system cluster 202 further includes an optical scatterometer 212 and a spectroscopic ellipsometer (SE) 214, to which a robot 216 may selectively provide wafers according to one or more selection criteria, as illustrated and described hereinabove. As noted above, optical scatterometer 212 may comprise spectroscopic ellipsometer 214. Optical scatterometer 212 may also comprise a reflectometer.

Wafers are provided to the robot 216 by an unload station 220, for example, which unloads the wafers from a wafer holding device such as a cassette (not shown), and once appropriate measurements have been made in the integrated system 202, the wafers may be loaded into appropriate cassettes at a loading station 222. As with the measurement systems illustrated and described above, the robot 216 of the system 202 selectively provides wafers to one or more of the component measurement systems or instruments 210, 212, and/or 214 according to at least one selection criterion, such as capabilities requirements information associated with the processed wafers, as well as capability information, availability information, and throughput information associated with the measurement systems 210, 212, and 214.

There are many alternative arrangements, each having different strategies for loading and unloading wafers, as described above in conjunction with FIG. 1.

The capabilities information can comprise information indicating the type of feature(s) or dimension(s) to be measured in the system 202, as well as the required accuracy for the measurement(s). The selection takes into account the measurement capabilities of the systems 210, 212, and/or 214. For example, one or more of the systems 210, 212, and/or 214 may be capable of performing a given measurement within the required accuracy, while others may not. In addition, the respective systems 210, 212, and/or 214 each have different throughput capabilities. For instance, the SEM 210 can measure about 30 wafers per hour (wph), the scatterometer 212 can measure up to 150 wph, and the spectroscopic ellipsometer 214 may measure 75 to 80 wph. In accordance with an aspect of the invention, the robot 216 provides the wafers to the measurement instrument which can provide the highest throughput, within the required measurement capabilities for a particular measurement task. In this regard, the measurement capability requirements can be derived from the identity of a particular wafer, which can be obtained, for example, using an OCR system (not shown) or other identification device or technique.

In this regard, the selection may also take into account the availability or current utilization of the instruments 210, 212, and/or 214 in scheduling the transfer of wafers via the robot 216. Thus, the robot 216 can provide a wafer to a selected measurement system 210, 212, or 214 having capabilities required for the wafer according to the capabilities requirements information (e.g., obtained or derived from the wafer identification) and the measurement system capability information (e.g., whether a particular instrument 210, 212, and/or 214 is capable of performing a particular measurement). Furthermore, the selection may reflect the measurement system 210, 212, and/or 214 having the highest throughput with the capabilities required for the wafer according to measurement system availability information and throughput information. Thus, where the high throughput scatterometer 212 is currently being used to measure another wafer, the robot 216 may advantageously provide a wafer to the CD-SEM 210, even though this may have lower throughput capability. Alternative arrangements with more load/unload stations afford additional flexibility in this regard for throughput and performance optimization.

In addition, the measurement systems 210, 212, and/or 214 may be cross-calibrated 217 in order to facilitate alternating or switching between the measurement systems. That is, calculated measurements generated by the scatterometer 212 may be correlated to resemble the calculated measurements provided by the CD-SEM 210. This cross-calibration 217 technique facilitates data interpretation to the extent that the measurements generated by the scatterometer 212 for production samples can be used interchangeably with those given by CD-SEM 210.

For example, a reference wafer (e.g., a focus-exposure matrix wafer or test wafer) is measured with an integrated optical scatterometer 212 and scatterometry linewidth measurements are calculated in real time or by using a database comparison approach or mathematical database comparison. For further description of the database approach, pending U.S. application Ser. No. 09/927,177 (Publication No. 2002/0038196 A1) entitled "Database Interpolation Method For Optical Measurement of Diffractive Microstructures" and filed on Mar. 28, 2002 is hereby incorporated by reference.

The wafer is also measured by the CD-SEM 210 to produce CD-SEM linewidth measurements. The relationship between the CD-SEM and the scatterometry line width measurements is mathematically analyzed and represented as a polynomial expression defining a continuous curve fit referred to as a correlation function. The correlation functions may vary from process step to process step (e.g., gate to contact) in the same fabrication process, so each process step may have its own correlation function. The scatterometer may then be employed to measure linewidths on new and unknown wafers. The scatterometry linewidth is calculated as described above by comparing them to theoretical calculations. The calculated linewidth can then be adjusted with the correlation function in order to become a closer match with results expected if the CD-SEM 210 was used.

Figure 6:
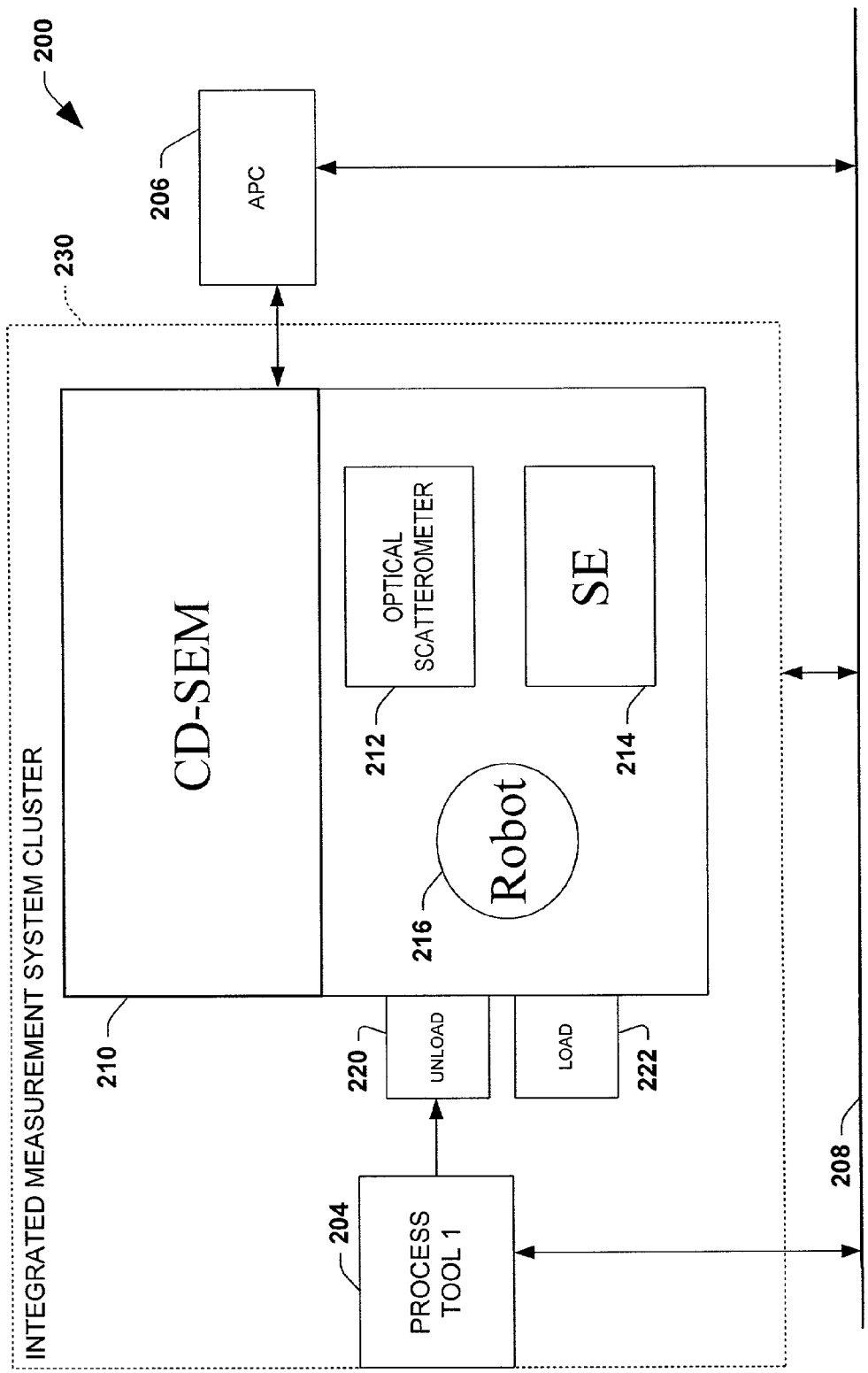
FIG. 6 is a schematic diagram illustrating another exemplary measurement system cluster in operative communication with a process tool.
Figure 7:
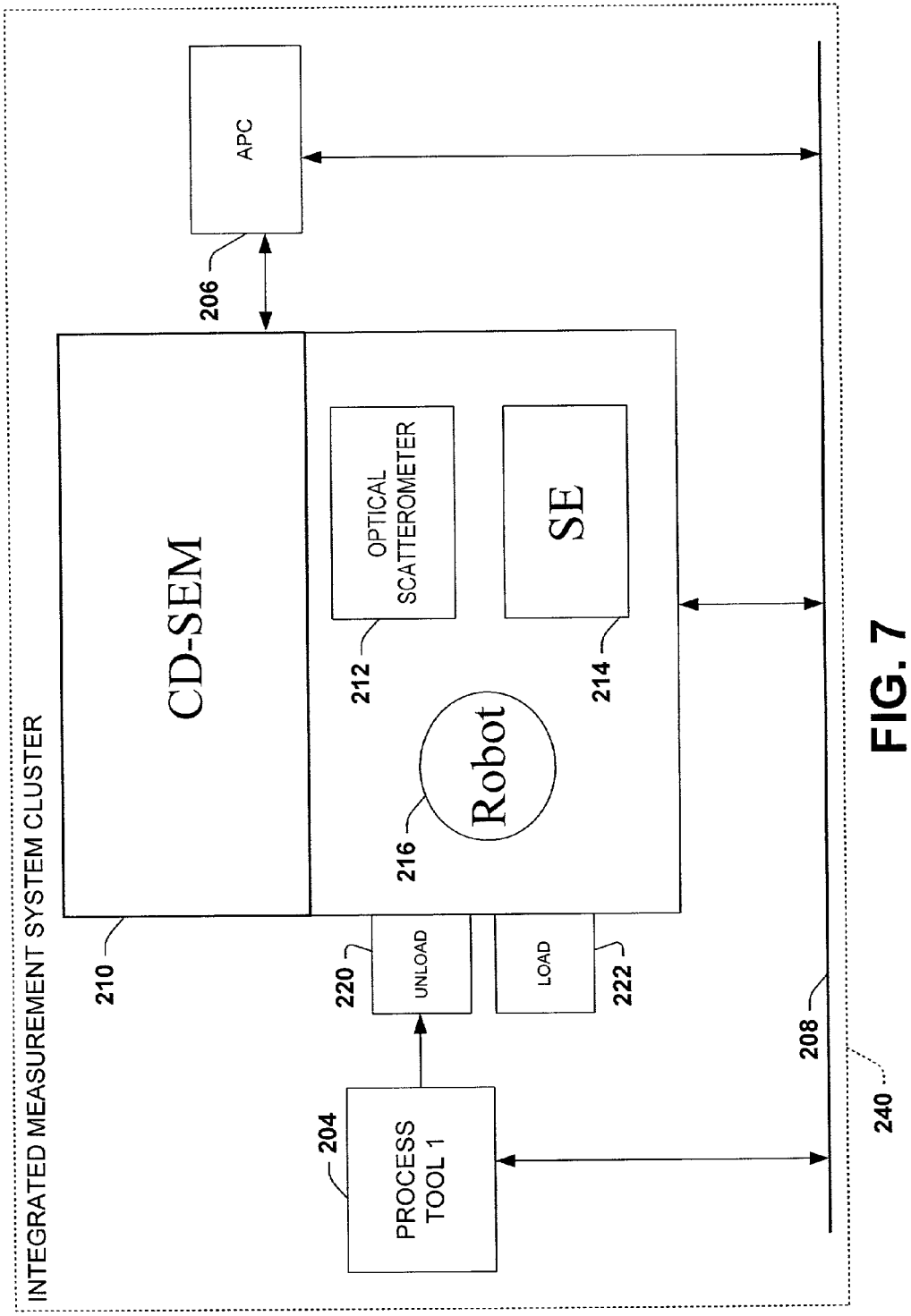
FIG. 7 is a schematic diagram illustrating another exemplary measurement system cluster integrated into a fabrication process with a process tool and an APC system.

Referring now to FIGS. 6 and 7, the invention also provides for integration of one or both of the APC system 206 and the process tool 204 with the measurement system cluster. For example, in FIG. 6, an integrated measurement system cluster 230 comprises the instruments 210, 212, and 214, the robot 216, and the unloading and loading stations 220 and 222. Another example is illustrated in FIG. 7, wherein an integrated system 240 comprises instruments 210, 212, and 214, the robot 216, unloading and loading stations 220 and 222, the APC system 206, and the process tool 204. In this example, it will be appreciated that the system 240 is not necessarily shown to scale, and that the process tool 204 may be physically much larger than the other components in the system 240, in which case the integration may take the form of attaching the clustered measurement components to the process tool 204. It will be further appreciated that the integration of such components may advantageously reduce or eliminate the excessive physical transfer (e.g., sometimes manual) of wafers from one component to another, and that the loading and unloading stations 222 and 220, respectively, may not be needed in the system 240, as wafers from the process tool 204 can be introduced directly to the robot 216.

The present invention thus provides for intelligent selection of measurement instrumentation in order to provide timely measurement and/or inspection information and other feedback information not previously achievable. One example of such intelligent selection is illustrated in FIG. 8, wherein an exemplary measurement system selection logic component 250 is illustrated. The logic component 250 may operate in similar fashion to the measurement selection logic component 34 of FIG. 1, as described hereinabove, whereby one or more selection criteria may be used in making a selection from among two or more measurement instruments or systems in a measurement system cluster (e.g., cluster 2 of FIG. 1). For example, the selection logic component 250 may be implemented in software, hardware, and/or combinations thereof, such as in a computer system (e.g., computer system 30 of FIG. 1).

The exemplary logic component 250 comprises various information used to provide a measurement system selection 252 to a wafer transfer system 254. For instance, capabilities requirements information 256 may be derived from a wafer identification 257, such as can be obtained from an optical scan of one or more characters or codes stamped on a wafer, for example, using an OCR system 258, as described above. The capabilities information 256 includes accuracies, and other parameters by which the selection logic component 250 may determine the suitability of one or more measurement instruments for a particular measurement or inspection task. For example, the logic component 250 may compare the capability requirements 256 for a particular task with measurement system capability information 261, 262, 263, and the like corresponding to measurement instruments (not shown) in a measurement system cluster (e.g., systems 10, 12, and 14 of FIG. 1), and determine which of the measurement systems meets the capability requirements 256.

In addition, the measurement system selection 252 may also be based on measurement system availability or utilization information 271, 272, 273, and the like corresponding with the measurement systems in the cluster. For example, the information 271, 272, and/or 273, and the like may be consulted or queried in order to ascertain whether an instrument is currently in use, about to be used, inoperable, scheduled for maintenance or the like. Thus, the wafer transfer system 254 may provide wafers to another measurement system where a first such system is currently in use, whereby parallel or simultaneous measurement operation of two or more measurement systems in a cluster may further speed up the measurement process from a cluster perspective. As a further consideration, the selection logic component 250 may consult measurement system throughput information 281, 282, 283, and the like in order to advantageously select an available measurement system having the highest throughput capability. In a further addition, the measurement system selection 252 may also be based on anticipated need based on fabrication schedule 260, e.g., for a fabrication process 80 as shown in FIG. 3. Fabrication schedule 260 may include information to allow intelligent sampling of the performance of particular process tools, e.g., 76 and 79.

Figure 9:
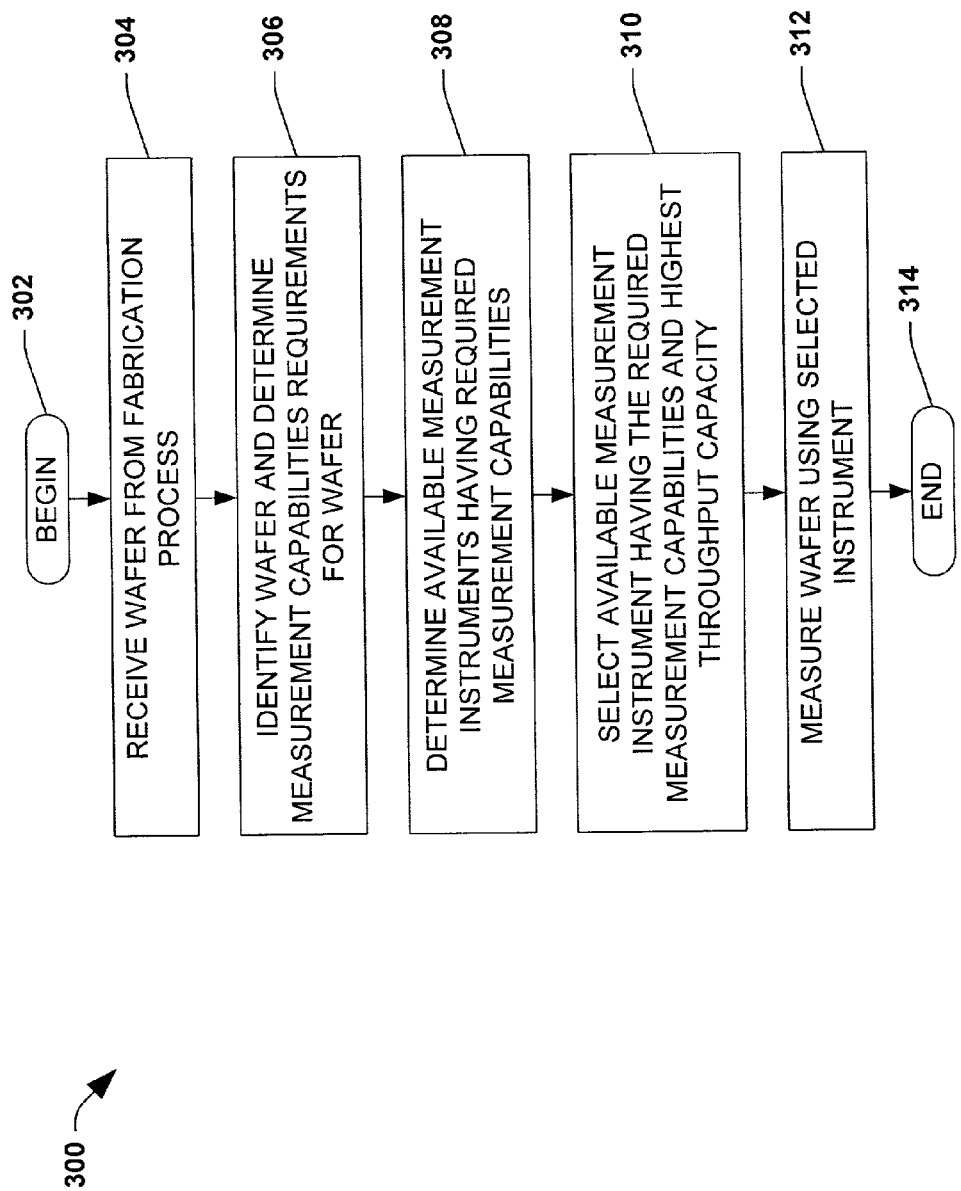
FIG. 9 is a flow diagram illustrating an exemplary methodology in accordance with the invention.

Another aspect of the invention provides methodologies for measuring process parameters in a semiconductor fabrication process. Referring now to FIG. 9, and exemplary method 300 is illustrated in accordance with the invention. Although the exemplary method 300 is illustrated and described herein as a series of blocks representative of various events and/or acts, the present invention is not limited by the illustrated ordering of such blocks. For instance, some acts or events can occur in different orders and/or concurrently with other acts or events, apart from the ordering illustrated herein, in accordance with the invention. Moreover, not all illustrated blocks, events, or acts, may be required to implement a methodology in accordance with the present invention. In addition, it will be appreciated that the exemplary method 300 and other methods according to the invention can be implemented in association with the apparatus and systems illustrated and described herein, as well as in association with other systems and apparatus not illustrated or described.

Beginning at 302, a wafer is received at 304 from a fabrication process. For example, a wafer may be received in a measurement system cluster (e.g., system 2 of FIG. 1) from a process tool. At 306, the wafer is identified (e.g., using an OCR system to read at least one character thereon or by some other technique), and the measurement capabilities requirements therefor are determined. Thereafter at 308, a determination is made as to available measurement instruments (e.g., component measurement devices in a measurement system cluster) having the required measurement capabilities. Such determination may take into consideration the anticipated need based on the fabrication schedule. At 310, an available measurement instrument is selected having the required measurement capabilities and having the highest throughput capacity. The wafer is then measured at 312 using the measurement system or instrument selected at 312, whereafter the method 300 ends at 314.

Although the invention has been shown and described with respect to certain illustrated implementations, it will be appreciated that equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure, which performs the function in the herein illustrated exemplary aspects of the invention. In this regard, it will also be recognized that the invention may include one or more computer systems as well as computer-readable media having computer-executable instructions for performing the acts and/or events of the various methods of the invention. Various modes of communication, e.g., between components of a computer system or between systems, are in some cases implicit.

In addition, while a particular feature of the invention may have been disclosed with respect to only one of several implementations, such feature may be combined with one or more other features of the other implementations as may be desired and advantageous for any given or particular application. Furthermore, to the extent that the terms "includes", "including", with, "has", "having", and variants thereof are used in either the detailed description or the claims, these terms are intended to be inclusive in a manner similar to the term "comprising."

What is claimed is:

1. A system for creating setup information for use in measuring process parameters associated with semiconductor wafers in a semiconductor device manufacturing process, comprising:
    a stand-alone measurement instrument adapted to measure a wafer; and
    a setup information generator operatively associated with the stand-alone measurement instrument to create setup information according to a measurement therefrom and to provide the setup information to a process measurement system associated with the semiconductor device manufacturing process;
    wherein the setup information is usable by the process measurement system to measure process parameters associated with semiconductor wafers in the semiconductor device manufacturing process.

2. The system of claim 1, wherein the setup information comprises at least one of a recipe and a database.

3. The system of claim 1, wherein the setup information comprises a recipe.

4. The system of claim 1, wherein the setup information comprises a database.

5. The system of claim 1, wherein the setup information comprises defect information.

6. The system of claim 1, wherein the stand-alone measurement instrument is networked to the process measurement system.

7. The system of claim 1, wherein the stand-alone measurement instrument includes at least one of a reflectometer and an ellipsometer.

8. The system of claim 1, wherein said process measurement system is integrated with a process tool.

9. The system of claim 1, wherein said process measurement system is a measurement cluster with at least two different measurement instruments.

10. A method of fabricating semiconductor wafers comprising the steps of:
    measuring a wafer in a stand-alone measurement instrument to develop a database of information related thereto;
    supplying the database information to a process measurement system;
    processing a wafer in a process tool; and
    measuring the wafer with a measurement system associated with the process tool and using the database information supplied from the stand-alone measurement instrument.

11. A method as recited in claim 10, wherein said stand-alone measurement instrument is networked to said process measurement system.

12. A method as recited in claim 10, wherein said process measurement system is integrated with the process tool.

13. A system for fabricating a semiconductor wafer comprising:
    a wafer process tool;
    a process measurement instrument associated with the process tool for measuring wafers after emerging from the process tool; and
    a stand-alone measurement system for measuring wafers and generating database information related thereto, said database information being supplied to the process measurement instrument to aid in measuring the wafers after processing.

14. A system as recited in claim 13, wherein said process measurement instrument is integrated with the process tool.

15. A system as recited in claim 13, wherein said stand-alone measurement system is networked to the process measurement instrument.

16. A system for fabricating a semiconductor wafer comprising:
- a wafer process tool;
- a process measurement cluster associated with the process tool for measuring wafers after emerging from the process tool, said measurement cluster including at least two different measurement instruments; and
- a stand-alone measurement system for measuring wafers and generating database information related thereto, said stand-alone measurement system including at least two measurement instruments of the type in the process measurement cluster, said database information being supplied to the process measurement cluster to aid in measuring the wafers after processing.

17. A system as recited in claim 16, wherein said process measurement cluster is integrated with the process tool.

18. A system as recited in claim 16, wherein said stand-alone measurement system is networked to the process measurement cluster.

* * * * *